US 6,540,981 B2

(12) United States Patent
Klaveness et al.

(10) Patent No.: US 6,540,981 B2
(45) Date of Patent: Apr. 1, 2003

(54) LIGHT IMAGING CONTRAST AGENTS

(75) Inventors: Jo Klaveness, Nycoveien (NO); Bjorn Fuglass, Nycoveien (NO); Pål Rongved, Nycoveien (NO); Edvin Johannesen, Nycoveien (NO); Paul Mark Hendrichs, Wayne, PA (US); Wolfgang Hans Heinrich Gunther, Wayne, PA (US); Edward Richard Bacon, Wayne, PA (US); John Luke Toner, Wayne, PA (US); Gregory Lynn McIntire, Wayne, PA (US); Vinay C. Desai, Phoenixville, PA (US)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 09/732,917

(22) Filed: Dec. 11, 2000

(65) Prior Publication Data
US 2001/0022963 A1 Sep. 20, 2001

Related U.S. Application Data

(63) Continuation of application No. 08/984,771, filed on Dec. 4, 1997, now Pat. No. 6,159,445, which is a continuation-in-part of application No. 08/875,645, filed as application No. PCT/GB96/00222 on Feb. 2, 1996, now abandoned.

(51) Int. Cl.$^7$ .............................................. A61K 49/00
(52) U.S. Cl. ........................................ 424/9.6; 424/9.1
(58) Field of Search ....................... 424/9.1, 9.4, 9.45, 424/9.451, 9.6, 9.7; 600/300, 310, 317

(56) References Cited

U.S. PATENT DOCUMENTS

| 3,806,592 A | 4/1974 | Imondi .......................... 424/7 |
| 4,808,399 A | 2/1989 | Rtpacek et al. ................. 424/2 |
| 5,093,106 A | 3/1992 | Dzbanovsky et al. ......... 424/7.1 |
| 5,140,463 A | 8/1992 | Yoo et al. .................... 359/559 |
| 5,437,274 A | 8/1995 | Khoobehi et al. |
| 5,460,800 A | 10/1995 | Walters |
| 5,498,421 A | 3/1996 | Grinstaff et al. ............. 424/450 |
| 5,505,932 A | 4/1996 | Grinstaff et al. ............. 424/9.3 |
| 5,508,021 A | 4/1996 | Grinnstaff et al. ........ 424/9.322 |
| 5,512,268 A | 4/1996 | Grinstaff et al. ......... 424/9.322 |

FOREIGN PATENT DOCUMENTS

| EP | 0 446 028 A3 | 6/1991 |
| EP | 0 446 028 A2 | 6/1991 |
| GB | 2 184 015 A | 6/1987 |

OTHER PUBLICATIONS

Bjerknes, et al., "Human Leukocyte Phagocytosis of Zymosan Particles Measured by Flow Cytometry", Acta path.microbiol.immunol.scand. Sect. C, 91:341–348, 1983.

Cheng, et al., "The Production and Evaluation of Contrast–Carrying Liposomes Made with an Automatic High–Pressure System", Investigative Radiology, 22:47–55, 1997.

Jain, "Barrier to Drug Delivery in Solid Tumors", Scientific American, pp. 58–65, Jul. 1994.

*Primary Examiner*—Michael G. Hartley
(74) *Attorney, Agent, or Firm*—Fish & Richardson P.C.

(57) ABSTRACT

The present invention relates to the use of particulate materials as contrast agents in in vivo light imaging.

31 Claims, No Drawings

LIGHT IMAGING CONTRAST AGENTS

RELATED APPLICATIONS

This application is a continuation of U.S. application Ser. No. 08/984,771, filed Dec. 4, 1997, U.S. Pat. No. 6,159,445, which is a continuation-in-part of application Ser. No. 08/875,645 filed Jul. 31, 1997, now abandoned, as the US designation of International patent application No. PCT/GB96/00222 filed Feb. 2, 1996.

FIELD OF THE INVENTION

The present invention relates to the use of particulate contrast agents in various diagnostic imaging techniques based on light, more particularly to particulate light imaging contrast agents.

BACKGROUND OF THE INVENTION

Contrast agents are employed to effect image enhancement in a variety of fields of diagnostic imaging, the most important of these being X-ray, magnetic resonance imaging (MRI), ultrasound imaging and nuclear medicine. Other medical imaging modalities in development or in clinical use today include magnetic source imaging and applied potential tomography. The history of development of X-ray contrast agents is almost 100 years old.

The X-ray contrast agents in clinical use today include various water-soluble iodinated aromatic compounds comprising three or six iodine atoms per molecule. The compounds can be charged (in the form of a physiologically acceptable salt) or non-ionic. The most popular agents today are non-ionic substances because extensive studies have proven that non-ionic agents are much safer than ionics. This has to do with the osmotic loading of the patient. In addition to water-soluble iodinated agents, barium sulphate is still frequently used for X-ray examination of the gastrointestinal system. Several water-insoluble or particulate agents have been suggested as parenteral X-ray contrast agents, mainly for liver or lymphatic system imaging. Typical particulate X-ray contrast agents for parenteral administration include for example suspensions of solid iodinated particles, suspensions of liposomes containing water-soluble iodinated agents or emulsions of iodinated oils.

The current MRI contrast agents generally comprise paramagnetic substances or substances containing particles (hereinafter "magnetic particles") exhibiting ferromagnetic, ferrimagnetic or superparamagnetic behaviour. Paramagnetic MRI contrast agents can for example be transition metal chelates and lanthanide chelates like Mn EDTA and Gd DTPA. Today, several gadolinium based agents are in clinical use; including for example Gd DTPA (Magnevist®), Gd DTPA-BMA (Omniscan®), Gd DOTA (Dotarem®) and Gd HPDO3A (Prohance®). Several particulate paramagnetic agents have been suggested for liver MRI diagnosis; for example suspensions of liposomes containing paramagnetic chelates and suspensions of paramagnetic solid particles like for example gadolinium starch microspheres. Magnetic particles proposed for use as MR contrast agents are water-insoluble substances such as $Fe_3O_4$ or $\delta\text{-}Fe_2O_3$ optionally provided with a coating or carrier matrix. Such substances are very active MR contrast agents and are administered in the form of a physiologically acceptable suspension.

Contrast agents for ultrasound contrast media generally comprise suspensions of free or encapsulated gas bubbles. The gas can be any acceptable gas for example air, nitrogen or a perfluorocarbon. Typical encapsulation materials are carbohydrate matrices (e.g. Echovist® and Levovist®), proteins (e.g. Albunex®), lipid matrials like phospholipids (gas-containing liposomes) and synthetic polymers.

Markers for diagnostic nuclear medicine like scintigraphy generally comprise radioactive elements like for example technetium (99m) and indium (III), presented in the form of a chelate complex, whilst lymphoscintigraphy is carried out with radiolabelled technetium sulphur colloids and technetium oxide colloids.

The term "light imaging" used here includes a wide area of applications, all of which utilize an illumination source in the UV, visible or IR regions of the electromagnetic spectrum. In light imaging, the light, which is transmitted through, scattered by or reflected (or re-emitted in the case of fluorescence) from the body, is detected and an image is directly or indirectly generated. Light may interact with matter to change its direction of propagation without significantly altering its energy. This process is called elastic scattering. Elastic scattering of light by soft tissues is associated with microscopic variations in the tissue dielectric constant. The probability that light of a given wavelength ($\lambda$) will be scattered per unit length of travel in tissue is termed the (linear) scattering coefficient $\mu_s$. The scattering coefficient of soft tissue in an optical window of approx. 600–1300 nm ranges from $10^1$–$10^3$ $cm^{-1}$ and decreases as $1/\lambda$. In this range $\mu_s \gg \mu_a$ (the absorption coefficient) and although $\mu_s$ (and the total attenuation) is very large, forward scattering gives rise to substantial penetration of light into tissue. Ballistic light is light that has travelled through a region of tissue without being scattered. Quasi-ballistic light ("snake" light) is scattered light that has maintained approximately the same direction of travel. The effective penetration depth shows a slow increase or is essentially constant with increasing wavelengths above 630 nm (although a slight dip is observed at the water absorption peak at 975 nm). The scattering coefficient shows only a gradual decrease with increasing wavelength.

Light that is scattered can either be randomly dispersed (isotropic) or can scatter in a particular direction with minimum dispersion (anisotropic) away from the site of scattering. For convenience and mathematical modelling purposes, scattering in tissue is assumed to occur at discrete, independent scattering centers ("particles"). In scattering from such "particles", the scattering coefficient and the mean cosine of scatter (phase function) depend on the difference in refractive index between the particle and its surrounding medium and on the ratio of particle size to wavelength. Scattering of light by particles that are smaller than the wavelength of the incident light is called Rayleigh scattering. This scattering varies as $1/\lambda^4$ and the scattering is roughly isotropic. Scattering of light by particles comparable to or larger than the wavelength of light is referred to as Mie scattering. This scattering varies as $1/\lambda$ and the scattering is anisotropic (forward peaked). In the visible/near-IR where most measurements have been made, the observed scattering in tissue is consistent with Mie-like scattering by particles of micron scale: e.g. cells and major organelles.

Since the scattering coefficient is so large for light wavelengths in the optical window (600–1300 nm), the average distance travelled by a photon before a scattering event occurs is only 10–100 $\mu$m. This suggests that photons that penetrate any significant distance into tissue encounter multiple scattering events. The ballistic component of light that has travelled several centimeters through tissue is exceedingly small. Multiple scattering in tissue means that the true optical path length is much greater than the physical distance between the light input and output sites. The scattering acts, therefore, to diffuse light in tissue (diffuse-transmission and -reflection). The difficulty that multiple scattering presents to imaging is three-fold: (i) light that has been randomized due to multiple scattering has lost signal information and contributes noise to the image (scattering increases noise); (ii) scattering keeps light within tissue for a greater period of time, increasing the probability for absorption, so less light transmits through tissue for detection (scattering decreases signal); and (iii) the determination of physical properties of tissue (or contrast media) such as concentration that could be obtained from the Beer-Lambert law is complicated since the true optical path length due to scattering is difficult to determine (scattering complicates the quantification of light interactions in tissue). However, although light cannot penetrate more than a few tens of microns in tissue without being scattered, the large value of the mean cosine of scattering indicates that a significant fraction of photons in an incident beam may undergo a large number of scatters without being deviated far from the original optical axis, and as such can contribute in creating an image. As a result, it can be possible to perform imaging on tissue despite the predominance of scatter, if the noise component can be rejected and the quasi-ballistic component of the light can be detected.

The most interesting wavelengths for light imaging techniques are in the approximate range of 600–1300 nm. These wavelengths have the ability to penetrate relatively deeply into living tissue without absorption by natural substances and furthermore are harmless to the human body. However, for optical analysis of surface structures or diagnosis of diseases very close to the body surface or body cavity surfaces or lumens, UV light and visible light below 600 nm wavelength can also be used.

Light can also be used in therapy; thus for example in Photodynamic Therapy (PDT) photons are absorbed and the energy is transformed into heat and/or photochemical reactions which can be used in cancer therapy.

The main methods of light imaging today include simple transillumination, various tomographic techniques, fluorescence imaging, and hybrid methods that involve irradiation with or detection of other forms of radiation or energy in conjunction with irradiation with or detection of light (such as photoacoustic or acousto-optical). These methods take advantage of either transmitted, scattered or emitted (fluorescence) photons or a combination of these effects. The present invention relates to contrast agents for any of these and further imaging methods based on any form of light.

There is today great interest in development of new equipment for imaging based on light. Interesting methods are especially the various types of tomographic techniques in development especially in Japan. As scientific references to the use of light in diagnostic medicine and PDT see for example Henderson, B. and Dougherty, T. in Photodynamic Therapy. Basic Principles and Clinical Application (1992), Gonzalez, E. et al. in *Psoriasis* (1991) 519 and 603, *Scrip* 1815 (1993) 25, Andersson-Engeles, S. et al. in *Lasers in Medical Science* 4 (1988) 115, Andersson, P. et al. in *IEEE* 23 (1987) 1798, Andersson, P. et al. in *Lasers in Medical Science* 2 (1987) 261, Anderson, R. et al. in *Applied Optics* 28 (1989) 2256, Amato, I., in *Science* 260 (1993) 1234, Alfano, R. et al. in *IEEE* 20 (1984) 1512, Lipowska, M. et al. at *ACS Nat Meeting* (1991), *Clinica* 528 (1992) 17, Andersson-Engles, S. et al. in *Optics Letter* 15 (1990) 1179, Andersson-Engles, S. et al. in *Lasers in Medical Science* 4 (1989) 241, Andersson-Engels, S. et al. in *Lasers in Medical Science* 4 (1989) 171, Andersson-Engels, S. et al. in *IEEE* 26 (1990) 2207, Andersson-Engels, S. et al. in *Photochem and Photobiol* 53 (1991) 807, Andersson-Engels, S., et al. in *SPIE* 908 (1988) 116, Andersson-Engels, S. et al. in *SPIE* 1205 (1990) 179, Andersson-Engels, S. et al. in *Anal. Chem* 61 (1989) 1367 and in *Anal. Chem* 62 (1990) 19, Andreoni, A. in *Photochem and Photobiol* 52 (1990) 423, Ankerst, J. et al. in *Appl. Spectroscopy* 38 (1984) 890, Anthony, D. et al. in *Photochem and Photobiol.* 49 (1989) 583, Araki, R. et al. in *Time Resolved Spectroscopy and Imaging of Tissues* 1431 (1991) 321, Arnfield, M. et al. in *Photochem and Photobiol* 51 (1990) 667, Arridge, S. et al. in *Phys. Med. Biol* 37 (1992) 1531, Arridge, S. et al. in *SPIE* 1431 (1991) 204, Balzani, S. et al. in *Photochem and Photobiol* 52 (1990) 409, Barabash, R. et al. in *IEEE* 26 (1990) 2226, Barker, D. et al. in *Br. J. Exp. Path* 51 (1970) 628, Baum, R. in *C&EN* October 31 (1988) 18, Baumgartner, R. et al. in *Photochem and Photobiol* 46 (1987) 759, Benaron, D. et al. in *Science* 259 (1993) 1463, Benson, R. et al. in *J. Chem. Eng. Data* 22 (1977) 379, Bickers, D. in *Invest Radiol* 21 (1986) 885, Blasdel, G. et al. in *Nature* 321 (1986) 579, Blasse, G. in *Photochem and Photobiol* 52 (1990) 417, Bolin, F. et al. in *Appl. Optics* 28 (1989) 2297, Boulnois, J. in *Lasers in Medical Science* 1 (1985) 47, Brodbeck, K. et al. in *Med. Phys* 14 (1987) 637, Carney, J. et al. in *Anal. Chem* 65 (1993) 1305, Chan, W. et al. in *Photochem and Photobiol* 50 (1989) 617, Chance, B. in *SPIE* 1641 (1992) 162, Chance, B. et al. in *SPIE* 1204 (1992) 481, Cheong, W. et al. in *IEEE* 26 (1990) 2166, Cope, M. et al. in *SPIE* 1431 (1991) 251, Deckelbaum, L. et al. in *Lasers in Surgery and Medicine* 7 (1987) 330, Delpy, D. et al. in *Phys Med Biol* 33 (1988) 1433, Detty, M. et al. in *JACS* 112 (1990) 3845, Detty, M. et al. in *J. Med. Chem* 33 (1990) 1108, Doiron, D. in *Prog. in Clin & Biol. Res* 170 (1984) 41, Driver, I. in *Phys. Med. Biol* 36 (1991) 805, Feather, J. et al. in *Lasers in Medical Science* 5 (1990) 345, Fishkin, J. et al. in *SPIE* 1431 (1991) 122, Flock, S. in *Med. Phys.* 14 (1987) 835, Gathje, J. et al. in *Applied Physiology* 29 (1970) 181, Gomer, C. et al. in *Cancer Research* 50 (1990) 3985, Gruribaum, F. et al. in *SPIE* 1431 (1991) 1431, Haglund, M. et al. in *Nature* 358 (1992) 668, Hebden, J. et al. in *Am. Assoc. Phys. Med.* 19 (1992) 1081, Hebden, J. et al. in *Med. Phys.* 17 (1990) 41, Hoek, A. V. et al. in *IEEE* 23 (1987) 1812, Hohla, K. et al. in *SPIE* 908 (1988) 128, Holbrooke, D. et al. in *Proc. N.Y. Ac Sci* 267 (1976) 295, Hoyt, C. et al. in *Lasers in Surgery and Medicine* 8 (1988) 1, Huang, D. et al. in *Science* 254 (1991) 1178, Jacson, P. et al. in *Invest Radiol.* 20 (1985) 226, Jacques, S. et al. in *Lasers in the Life Science* 1 (1987) 309, Kittrell, C. et al. in *Applied Optics* 24 (1985) 2280, Lakowicz, J. in *Biophys J.* 46 (1984) 463, Lam, S. et al. in *Chest* 97 (1990) 333, Li, W. in *Opthalmology* 100 (1982) 484, Lilge, L. et al. in *SPIE* 1203 (1990) 106, Lytle, A. et al. in *SPIE* 1200 (1990) 466, MacVicar, B. et al. in *J. Neuroscience* 11 (1991) 1458, Maijnissen, J. et al. in *Lasers in Surgery and Medicine* 2 (1987) 235, Marynissen, J. et al. in *J. Urology* 142 (1989) 1351 and *Prog. in Clin & BioRes* 170 (1984) 133. McCormick, P. et al. in *Critical Care Medicine* 19 (1991) 89, Mcormick, P. et al. in *J. Neurosurg* 76 (1992) 315, McKenzie, A. et al. in *Phys. Med. Biol.* 30 (1985) 455, Moes, C. et al. in *Applied Optics* 28 (1989) 2292, Montan, S. et al. in *Optics Letters* 10 (1985) 56, Montforts, F. et al. in *Angev Chem* (Int. Ed.) 31 (1992) 1592, Morgan, A. et al. in *Photochem and Photobiol* 52 (1990) 987, Morgan, A. et al. in *J. Med. Chem* 33 (1990) 1258, Morgan, A. et al. in *J. Med. Chem* 32 (1989) 904, Navarro, G. et al. in *Med. Phys.* 15 (1988) 181, Nelson, J. et al. in *Cancer Research* 4 (1987) 4681, Orbach, H. et al. i *J. Neuroscience* 5 (1985) 1886, Pandey, R. et al. in *Chem. Lett.* 2 (1992) 491, Parker, F. et al. in *Analyt. Biochem* 18 (1967) 414, Parrish, J. in *J. Derm* 17 (1990) 587, Parrish, J. et al. in *Photochem and Photobiol* 53 (1991) 731, Patterson, M. et al. in in *Appl. Optics* 28 (1989) 2331. Patterson, M. et al. in *SPIE* 1203 (1990) 62, Patterson, M. et al. in *SPIE* 1065 (1989) 115, Patterson, M. et al. in *Photosenziation* 15 (1988) 121, Patterson, M. et al. in *Lasers in Medical Science* 6 (1991) 379, Peters, V. et al. in *Phys. Med. Biol* 35 (1990) 1317, Profio, A. in *Photochem. and Photobiol* 46 (1987) 591, Profio, A. et al. in *Med. Phys* 11 (1984) 516, Prout, G. et al. in *New England Journal of Medicine* 317 (1987) 1251, Roberts, W. et al. in *J. Nat Cancer Inst* 80 (1988) 330, Rosenthal, I in *Photochem and Photobiol* 53 (1991) 559, Sartori, M. et al. in *IEEE* 23 (1987) 1794, Schmitt, J. in *Applied Optics* 31 (1992) 6535, Schmitt, J. et al. in *Opt. Soc. Am.* 7 (1990) 2141, Schneckenburger, H. et al. in *Optical Engineering* 31 (1992) 1447, Selman, S. et al. in *SPIE* 997 (1988) 12, Selman, S. et al. in *J. Urology* 143 (1990) 630, Sevick, E. et al. in *Anal. Biochem* 195 (1991) 330, Shen, N. et al. in *Pharmacologica Sinia* 4 (1986) 346, Shiner, W. et al. in *Photonics Spectra* September (1992) 109, Spears, K. et al. in *IEEE* 36 (1989) 1210, Spikes, J. in *Photochem and Photobiol* 43 (1986) 691, Star, W. et al. in *Lasers in Medical Science* 5 (1990) 107, Star, W. et al. in *Photochem and Photobiol* 46 (1987) 619, Steike, J. et al. in *J. Opt. Soc. Am.* 6 (1988) 813, Stekeil, W. in *J. Physiol* 198 (1960) 881, Sullivan, F. et al. in *Applied Radiology* January (1993) 26, Svaasand, L. et al. in *Med. Phys* 12 (1985) 455, Svaasand, L. et al. in *Lasers in Medical Science* 5 (1985) 589, Svaasand, L. et al. in Photochem and Photobiol 41 (1985) 73, Svaasand, L. et al. in *Photochem and Photobiol* 38 (1983) 293, Svanberg, K. et al. in *Cancer Research* 46 (1986) 3803, Svanberg, K. et al. in *Physica Scripta* 26 (1989) 90, Tam, A. in *Ultrasensitive Laser Spectroscopy* (1983) 72, Toida, M. et al. in *Electronics and Communications in Japan* 75 (1992) 137, Tsay, T. et al. in *SPIE* 1646 (1992) 213, Tsuchiya, A. et al. in *J. Urology* 130 (1983) 79, Unsold, E. et al. in *Lasers in Medical Science* 5 (1990) 207, Vergara, J. et al. in *Biophysical Journal* 59 (1991) 12, Vitkin, I. et al. in *J. Photochem Photobiol* 16 (1992) 235, Wang, L. et al. in *Optics & Photonics* 2 (1991) 38, Wang, L. et al. in Science 253 (1991) 769, Wang, L. et al. in *SPIE* 1431 (1991) 97, Watmough, D. in *Brit. J. Radiology* 55 (1982), Wilson, B. et al. in *Phys Med Biol* 31 (1986) 327, Wilson, B. et al. *Lasers in Medical Science* 1 (1986) 235, Wyatt, J. et al. in *J. Appl. Physiol* 68 (1990) 1086, Wyatt, J. et al. in *Archives of Disease in Childhood* 64 (1989) 953, Yoo, K. et al. in *Optics Letters* 16 (1991) 1068, Yoo, K. et al. in *Optics Letters* 15 (1990) 320.

There are several patent publications which relate to light imaging technology and to the use of various dyes in light imaging: a labeling fluorescent dye comprising hydroxy aluminium 2,3-pyrido cyanide in JP 4,320,456 (Hitachi Chem), therapeutic and diagnostic agent for tumors containing fluorescent labelled phthalocyanine pigment in JP 4288 022 (Hitachi Chem), detection of cancer tissue using visible native luminescence in U.S. Pat. No. 4,930,516 (Alfano R. et al.), method and apparatus for detection of cancer tissue using native fluorescence in U.S. Pat. No. 5,131,398 (Alfano, R. et al.), improvements in diagnosis by means of fluorescenct light emmision from tissue in WO 90/10219 (Andersson-Engels, S. et al.), fluorescent porphyrin and fluorescent phthalocyanine-polyethylene glycol, polyol, and saccharide derivatives as fluorescent probes in WO91/18006 (Diatron Corp), method of imaging a random medium in U.S. Pat. No. 5,137,355 (State Univ. of New York), tetrapyrrole therapeutic agents in U.S. Pat. No. 5,066,274 (Nippon Petrochemicals), tetrapyrrole polyaminomonocarboxylic acid in therapeutic agents in U.S. Pat. No. 4,977,177 (Nippon Petrochemicals), tetrapyrrole aminocarboxylic acids in U.S. Pat. No. 5,004,811 (Nippon Petrochemicals), porphyrins and cancer treatment in U.S. Pat. No. 5,162,519 (Efamol Holdings), dihydroporphyrins and method of treating tumors susceptible to necrosis in U.S. Pat. No. 4,837,221 (Efamol), parenterally administered zinc phthalocyanide compounds in form of liposome dispersion containing synthetic phospholipids in EP 451 103 (CIBA Geigy), apparatus and method for detecting tumors in U.S. Pat. No. 4,515,165 (Energy Conversion Devices), time and frequency domain spectroscopy determining hypoxia in WO92/13598 (Nim Inc), phthalocyanatopolyethylene glycol and phthalocyanato saccharides as fluorescent digoxin reagent in WO 91/18007 (Diatron), fluorometer in U.S. Pat. No. 4,877,965 (Diatron), fiberoptic fluorescence spectrometer in WO 90/00035 (Yale Univ.), tissue oxygen measuring system in EP 502,270 (Hamamatsu Photonics), method for determining bilirubin concentration from skin reflectance in U.S. Pat. No. 4,029, 084 (Purdue Research Foundation), bacteriochlorophyll-a derivative useful in photodynamic therapy in U.S. Pat. No. 5,173,504 (Health Research Inc), purified hematoporphyrin dimers and trimers useful in photodynamic therapy in U.S. Pat. No. 5,190,966 (Health Research Inc), drugs comprising porphyrins in U.S. Pat. No. 5,028,621 (Health Research Inc), hemoporphyrin derivatives and process of preparing in U.S. Pat. No. 4,866,168 (Health Research Inc), method to destroy or impair target cells in U.S. Pat. No. 5,145,863 (Health Research Inc), method to diagnose the presence or absence of tumor tissue in U.S. Pat. No. 5,015,463 (Health Research Inc), photodynamic therapeutic technique in U.S. Pat. No. 4,957,481 (U.S. Bioscience), apparatus for examining living tissue in U.S. Pat. No. 2,437,916 (Philip Morris and Company), transillumination method apparatus for the diagnosis of breast tumors and other breast lesions by normalization of an electronic image of the breast in U.S. Pat. No. 5,079,698 (Advanced Light Imaging Technologies), tricarbocyanine infrared absorbing dyes in U.S. Pat. No. 2,895,955 (Eastman Kodak), optical imaging system for neurosurgery in CA 2,048,697 (Univ. Techn. Int.), new porphyrin derivatives and their metallic complexes as photosensitizer for PDT in diagnosis and/or treatment of cancer in JP 323,597 (Hogyo,T), light receiving system of heterodyne detection and image forming device for light transmission image in EP 445,293 (Research Development Corp. of Japan), light receiving system of heterodyne detection and image forming device for light transmission image using light receiving system in WO 91/05239 (Research Development Corp. of Japan), storage-stable porphyrin compositions and a method for their manufacture in U.S. Pat. No. 4,882,234 (Healux), method for optically measuring chemical analytes in WO 92/19957 (Univ. of Maryland at Baltimore), wavelength-specific cytotoxic agents in U.S. Pat. No. 4,883,790 (Univ. of British Columbia), hydromonobenzo-porphyrin wavelength-specific cytotoxic agents in U.S. Pat. No. 4,920,143 (Univ. of British Columbia), apparatus and method for quantitative examination and high-resolution imaging of human tissue in EP 447,708 (Haidien Longxing Med Co), optical imaging system for neurosurgery in U.S. Pat. No. 7,565,454 (University Technologies Int. Inc.), —characterization of specific drug receptors with fluorescent ligands in WO 93/03382 (pharmaceutical Discovery Corp), 4,7-dichlorofluorescein dyes as molecular probes in U.S. Pat. No. 5,188,934 (Applied Biosystems), high resolution breast imaging device utilizing non-ionizing radiation of narrow spectral bandwith in U.S. Pat. No. 4,649,275 (Nelson, R. et al.), meso-tetraphenyl-porphyrin-Komplexverbindungen, Verfaren zu ihrer Herstellung und Diese Enthaltends Pharmazeutische Mittel in EP 336,879 (Schering), 13,17-propionsaure und propionsaurederivat Substituerte Porphyrin-Komplexverbindungen, Verfahren zu ihrer Herstellung und diese Enthaltende Pharmazeutische Mittel in EP 355,041 (Schering), photosensitizing agents in U.S. Pat. No. 5,093, 349 (Health Research), pyropheophorbides and their use in photodynamic therapy in U.S. Pat. No. 5,198,460 (Health Research), optical histochemical analysis, in vivo detection and real-time guidance for ablation of abnormal tissues using Raman spectroscopic detection system in WO 93/03672 (Redd, D.), tetrabenztriazaporphyrin reagents and kits containing the same in U.S. Pat. No. 5,135,717 (British Technology Group), system and method for localization of functional activity in the human brain in U.S. Pat. No. 5,198,977 (Salb, J.). photodynamic activity of sapphyrins in U.S. Pat. No. 5,120,411 (Board of Regents, University of Texas), process for preparation of expanded porphyrins in U.S. Pat. No. 5,152,509 (Board of Regents, University of Texas), expanded porphyrins (Board of Regents, University of Texas), infrared radiation imaging system and method in WO 88/01485 (Singer Imaging), imaging using scattered and diffused radiation in WO 91/07655 (Singer Imaging), diagnostic apparatus for intrinsic fluorescence of malignant tumor in U.S. Pat. No. 4,957,114, indacene compounds and methods for using the same in U.S. Pat. No. 5,189,029 (Bo-Dekk Ventures), method of using 5,10,15,20-tetrakis (carboxy phenyl) porphine for detecting cancers of the lung in U.S. Pat. No. 5,162,231 (Cole, D. A. et al.), Verfahren zur Abbildung eines Gewebebereiches in DE 4327 798 (Siemens), chlorophyll and bacteriochlorophyll derivatives, their preparation and pharmaceutical compositions comprising them in EPO 584 552 (Yeda Research and Development Company), wavelength-specific photosensitive porphacyanine and expanded porphyrin-like compounds and methods for preparation and use thereof in WO 94/10172 (Qudra Logic Technologies), method and apparatus for improving the signal to noise ratio of an image formed of an object hidden in or behind a semiopaque random media in U.S. Pat. No. 5,140,463 (Yoo, K. M. et al.), benzoporphyrin derivatives for photodynamic therapy in U.S. Pat. No. 5,214,036 (University of British Columbia), fluorescence diagnostics of cancer using delta-amino levulinic acid in WO 93/13403 (Svanberg et al.), Verfahren zum Diagnostizieren von mit fluoreszierenden Substansen angereicherten, inbesondere tumorösen Gewebebereichen in DE 4136 769 (Humboldt Universität), terpyridine derivatives in WO 90/00550 (Wallac).

All the light imaging dyes or contrast agents described in the state-of-the-art have different properties, but all those agents have an effect on the incident light, leading to either absorption and/or fluorescence. However none of these contrast agents is used as a particulate contrast agent.

SUMMARY OF THE INVENTION

We have now found that contrast enhancement may be achieved particularly efficiently in light imaging methods by introducing particulate materials as scattering contrast agents. For the sake of clarity, the word "particle" is used to refer to any physiologically acceptable particulate materials. Such particles may be solid (e.g. coated or uncoated crystalline materials) or fluid (e.g. liquid particles in an emulsion) or may be aggregates (e.g. fluid containing liposomes). Particulate material with a particle size smaller than or similar to the incident light wavelength are preferred.

Thus viewed from one aspect the invention provides the use of a physiologically tolerable particulate material for the manufacture of a particulate-contrast-agent containing contrast medium for use in in vivo dignostic light imaging.

Viewed from a further aspect the invention also provides a method of generating an image of the human or non-human (preferably mammalian, avian or reptilian) animal body by light imaging, characterised in that a contrast effective amount of a physiologically tolerable particulate contrast agent is administered to said body, and an image of at least part of said body is generated. In such a method a contrast effective amount of the particulate agent is administered, e.g. parenterally or into an externally voiding body organ or duct, light emitted, transmitted or scattered by the body is detected and an image is generated of at least part of the body in which the contrast agent is present. Hybrid methods in which light, either alone or in conjunction with other forms of radiation, is administered to the body, and light, or some other form of radiation, is detected. In particular, the other form of radiation may be ultrasound.

DETAILED DESCRIPTION OF THE INVENTION

The particles used according to the invention are preferably water-insoluble or at least sufficiently poorly soluble as to retain their desired particle size (e.g. 600–1300 nm) for at least 2 hours following administration into the body under investigation.

The images generated may be spatial or temporal and mono- or multi-dimensional.

In a further aspect of the invention, the imaging technique may be used to determine a value for a parameter characteristic of the body or the part of the body under study, e.g. blood flow rate. In this case however, the parameter determination should be based on light detected from particles studied through the skin or through an endoscopically or surgically exposed surface.

Particularly preferably, the light imaging procedure used is selected from confocal scanning laser microscopy (CSLM), optical coherence tomography (OCT), laser doppler, laser speckle, and multi-photon microscopy techniques (for a description of the latter see for example Denk, W. in *Photonics Spectra* (1997) July 125–130, Denk, W. et al. in *Science* (1990) April 248 73–76, Denk, W. et al. in *J.Neurosci.Meth.* (1994) 54:2:151–162, Denk, W. et al. in *Neuron* (1997) January 18:351–357, Maiti, S. et al. in *Science* (1997) January 275 530–532 and Denk, W. et al. in *Proc. Natl. Acad.* (1995) August 92:18:8279–8282).

Confocal scanning laser microscopy (CSLM) is an imaging modality that selectively detects a single point within a test object by focusing light from a pinhole source onto that point. The light transmitting past or reflecting from that point is refocused onto a second pinhole that filters out light coming from any other site in the object except the focal point. Raster scanning of the focus point through a plane passing through the sample generates a full image of that plane of points. Moving the pinholes and focusing apparatus back and forth from the sample selects out different sample planes. In effect CSLM is a means for "optically" sectioning a test sample. It pulls out images of individual sections of the sample, but without the necessity that those sections be physically separated from the rest of the sample.

Optical coherence tomography (OCT) accomplishes optical sectioning in a related, but somewhat different manner. A collimated beam of light is reflected from the sample, then is compared with a reference beam that has travelled a precisely known distance. Only the light travelling exactly the same distance to the sample and back as the distance the reference beam travels from the source to the detector constructively interferes with the reference beam and is detected. Thus the light from a single plane within the sample is again selected. Varying the distance that the reference beam travels before it is compared with the sampling beam selects out different sample planes.

CSLM, OCT, laser doppler and laser speckle are discussed for example by: Rajadhyaksha et al. in Laser Focus World, February 1997, pages 119 to 127; Sabel et al. in Nature Medicine 3(2): 244–247 (1997); Tearney et al. in SPIE 2389: 29–34 (1995); Bonner et al. in "Scattering techniques applied to supramolecular and non-equilibrium systems", pages 685–701, Ed. Chen et al., Plenum; Ruth in J. Microcirc: Clin Exp 9: 21–45 (1990); Pierard in Dermatology 186: 4–5 (1993); and Bonner et al. in "Laser-dopper blood flowmetry" pages 17 to 46, Ed. Shepherd et al., Kluwer, 1990.

CSLM and OCT may be used particularly effectively to study structures and events occurring in the skin or within about a millimeter of an accessible surface of the body under study, e.g. a surface exposed during surgical operation or exposed endoscopically.

CSLM and OCT can be useful in optically guided tumor resection. For example, either device attached to a colonoscope may facilitate determination that no residual malignant tissue remains after removal of a cancerous colon polyp. Additional applications include, but are not limited to, diagnosis and treatment of disease in the rest of the digestive tract, surgical treatment of ulcerative colitis, and diagnosis and treatment of endometriosis.

Dynamically, CSLM and OCT can be used to follow the movement of blood cells through the capillaries of the skin and other vascularized tissue lying within about a millimeter of an exposed surface. Potentially they can also be used in conjunction with laser Doppler or speckle inferferometry for the measure of blood flow.

Laser Doppler and speckle interferometry are related, each relying upon the fact that the intensity of light detected after a beam of laser light that interacts with a collection of moving particles changes with time. Mathematical analysis of the changes provides a basis for calculating the rate at which the particles are moving.

The perfusion of tissue that is exposed by surgery is one important indicator of the health of that tissue. Blood flow within the skin of the breast may be an indicator of internal disease. Blood flow in the skin can be detected by laser Doppler blood-flow measurement or laser speckle interferometry, either by itself or in conjunction with CSLM or OCT.

According to the present invention, synthetic particles, capable of scattering light of the wavelength used for the imaging procedure, may be administered as contrast agents in an in vivo light imaging procedure. Typically such scattering particles will be administered in suspension in a physiologically tolerable fluid (e.g. water for injections, physiological saline, Ringer's solution etc.) into the vasculature or musculature or into the tissue or organ of interest.

A preferred contrast agent for intraoperative CSLM or OCT will have the following properties: it will consist of stabilized particles in an aqueous or buffered liquid medium. The particle size will preferably be around 600 to 1300 nm, more preferably 700 to 1100 nm (i.e. roughly equal to the wavelength of the light source). The refractive index of the particles will preferably differ from that of body fluids, such as blood and lymph, by at least 0.01. Optionally the particles may have fluorescent dyes attached to their surfaces or contained within them or the particles themselves may be composed of fluorescent dyes. Optionally the particles may have suitable surface modifying agents, such as poly (ethylene glycol), to slow their uptake by macrophages in the body and to prolong their blood circulation lifetimes.

The particles may be of a material which is transparent or translucent or more preferably opaque to light of the wavelength of the light source.

Particularly preferably, the particles are substantially monodisperse polymer particles (with a coefficient of variation of the particle size (i.e. 100× standard deviation÷mean particle size by volume of the major mode of the detectable particles) as measured by a Coulter LS 130 particle size analyzer of less than 10%, preferably less than 5%). Such particles may be prepared by the SINTEF technique disclosed in U.S. Pat. No. 4,336,173 and U.S. Pat. No. 4,459,378. Such polymer particles may be simple scatterers or may be modified to carry a chromophore (or fluorophore), preferably having characteristic absorption and/or emission maxima in the 600 to 1300 nm range. Furthermore they may be modified to include or carry a targetting vector, e.g. a species serving to cause the particles to accumulate at a desired target site, for example superparamagnetic crystals which allow the particle to be accumulated at a target site by application of an external magnetic field, or a drug, antibody, antibody fragment or peptide (e.g. an oligopeptide or polypeptide) which has a binding affinity for sites within the target zone, e.g. cell surface receptors.

The particulate contrast agent can be applied through simple topical application or other pharmaceutically acceptable routes. For dermatological applications, the contrast agents may be modified to be delivered through transdermal patches or by iontophoretesis. Iontophoretic delivery is preferred, as one can control the amount of the agent that is delivered.

For intraoperative uses the contrast agent can be injected into the vasculature or into the lesion to be removed prior to or during the surgery. For detection of lymph nodes it can be injected into a lymph duct draining into the surgical area. Alternatively it may be applied during surgery as a topical ointment, a liquid, or a spray. For measurement of blood flow the agent can be injected intravascularly prior to the measurement.

As indicated above, the particulate agents used according to the invention may comprise a chromophore or fluorophore, i.e. may absorb or emit light in the wavelength range detected in the imaging procedure or alternatively may rely primarily upon light scattering effects. In the latter case, one may simply use physiologically tolerable non photo-labelled particles, e.g. particles of an inert organic or inorganic material, e.g. an insoluble triiodophenyl compound or titanium dioxide, which appears white or colourless to the eye. Where the particles comprise a fluorophore or chromophore, i.e. are photo-labelled, this may be in a material carried by (e.g. bound to, coated on, or contained or deposited within) a particulate carrier (e.g. a solid particulate or a liposome). Alternatively the carrier itself may have chromophoric or fluorophoric properties. While the photo-label may be a black photolabel (i.e. one which absorbs across the visible spectrum and thus appears black to the eye) non-black photolabels are preferred.

Scattering contrast agents (and absorbing contrast agents for that matter) can have several mechanisms in image enhancement for light imaging applications. The first mechanism is a direct image enhancing role similar to the effect that x-ray contrast media have in x-ray imaging. In direct image enhancement, the contrast medium contributes directly to an improvement in image contrast by affecting the signal intensity emanating from the tissue containing the contrast medium. In light imaging, scattering (and absorbing) agents localized in a tissue can attenuate light differently than the surrounding tissue, leading to contrast enhancement.

For near surface methods such as confocal microscopy and optical coherence tomography, scattering agents generate contrast primarily by serving as reflection centres that selectively direct the incident light to the detector. When scattering sites are trapped in a moving fluid, such as blood, the extent of the scattering sites' movement can be used as a measure of the fluid's flow rate.

The "speckle" phenomenon results from the interaction of coherent radiation (such as that from a laser) with scattering sites. When the scattering sites move, the speckle pattern changes with time, and the rate of change of the speckle pattern can be used to determine the rate of movement of the scattering sites. If the movement of the scattering sites is non-random, for example when they are entrained in a moving fluid, the rate of fluid flow can be determined by the changes in the speckle pattern over time.

A second mechanism by which a scattering (or absorbing) agent could be used is as a noise rejection agent. The contrast agent in this case is not directly imaged as described above, but functions to displace a noise signal from an imaging signal so that the desired signal is more readily detected. Noise in light imaging applications results from multiple scattering and results in a degradation of image quality. The origin of this noise is as follows:

As previously mentioned, light propagating through a random medium such as tissue undergoes multiple scattering. This scattering splits the incident light into three components, the ballistic, quasi-ballistic, and incoherent (highly scattered) components. The ballistic and quasi-ballistic signals propagate through tissue in the forward direction and carry the object information. The incoherent component constitutes noise because the light has undergone random scattering in all directions and information about the object is lost. When the intensity of the ballistic and quasi-ballistic signals are reduced below the intensity of the multiply scattered noise, the object becomes invisible. This multiple scattering noise can be partially removed by a spatial filter that rejects light scattered away from the collinear direction of the incident light. However, a substantial portion of noise emerges from the object after multiple scattering events by rejoining the original ballistic signal. This multiply scattered light can not be removed by spatial filtering due to its collinear path with the desired ballistic signal.

Scattering (and absorbing) agents can aid in the removal of unwanted noise component from the desired ballistic and quasi-ballistic signals. This is based on the fact that multiply scattered light undergoes a random walk in tissue and thus travels over a longer path length than the ballistic signal. The distance the ballistic and quasi-ballistic signals traverses is essentially the thickness of the tissue (or body part) being imaged. Scattered light traveling a longer distance has a greater probability of being attenuated. Current technology uses a time-gate (temporal filter) to reject the scattered signal (longer traveling= longer residence time in tissue) from the ballistic and quasi-ballistic components.

The introduction of a small isotropic scattering agent greatly increases the residence time of the highly scattered signal component while having a lesser effect on the ballistic and quasi-ballistic components. This effectively provides a longer separation between the ballistic and quasi-ballistic signals and the highly scattered component, providing improved rejection of the scattered (noise) component and better image quality.

Very little is disclosed in prior art regarding particulate scattering-based contrast agents. To our knowledge the only prior art with regard to particulate scattering-based contrast agents is U.S. Pat. No. 5,140,463 (Yoo, K. M. et al.) which discloses a method and apparatus for improving the signal to noise ratio of an image formed of an object hidden in or behind a semi-opaque medium. The patent in general terms suggests to make the random medium less random (so that there will be less scattered light) and it is also suggested to increase the time separation between ballistic and quasi-ballistic light and the highly scattered light. One of many ways to obtain this will, according to the patent, be to introduce small scatterers into the random medium. There are no further suggestions regarding these small scatterers and no suggestion of in vivo use.

Particulate materials in the form of liposomes have been suggested; liposome or LDL-administered Zn(II)-phthalocyanine has been suggested as photodynamic agent for tumors by Reddi, E. et al. in *Lasers in Medical Science* 5 (1990) 339, parenterally administered zinc phtalocyanine compositions in form of liposome dispersion containing synthetic phopholipid in EP 451 103 (CIBA Geigy) and liposome compositions containing benzoporphyrin derivatives used in photodynamic cancer therapy or an antiviral agents in CA 2,047,969 (Liposome Company). These particulate materials have been suggested as therapeutic agents and have nothing to do with scattering light imaging contrast agents.

In one embodiment of the invention the contrast medium for imaging modalities based on light will comprise physiologically tolerable gas containing particles. Preferred are e.g. biodegradable gas-containing polymer particles, gas-containing liposomes or aerogel particles.

This embodiment of the invention includes, for example, the use in light imaging of particles with gas filled voids (U.S. Pat. No. 4,442,843), galactose particles with gas (U.S. Pat. No. 4,681,119), microparticles for generation of microbubbles (U.S. Pat. No. 4,657,756 and DE 3313947), protein microbubbles (EP 224934), clay particles containing gas (U.S. Pat. No. 5,179,955), solid surfactant microparticles and gas bubbles (DE 3313946), gas-containing microparticles of amylose or polymer (EP 327490), gas-containing polymer particles (EP 458079), aerogel particles (U.S. Pat. No. 5,086,085), biodegradable polyaldehyde microparticles (EP 441468), gas associated with liposomes (WO 9115244), gas-containing liposomes (WO 9222247), and other gas containing particles (WO 9317718, EP 0398935, EP 0458745, WO 9218164, EP 0554213, WO 9503835, DE 3834705, WO 9313809, WO 9112823, EP 586875, WO 9406477, DE 4219723, EP 554213, WO 9313808, WO 9313802, DE 4219724, WO 9217212, WO 9217213, WO 9300930, U.S. Pat. No. 5,196,183, WO 9300933, WO 9409703, WO 9409829, EP 535387, WO 9302712, WO 9401140). The surface or coating of the particle can be any physiologically acceptable material and the gas can be any acceptable gas or gas mixture. Specially preferred gases are the gases used in ultrasound contrast agents like for example air, nitrogen, lower alkanes and lower fluoro or perfluoro alkanes (e.g. containing up to 7, especially 4, 5 or 6 carbons).

Where gas microbubbles (with or without a liposomal encapsulating membrane) are used according to the invention, advantage may be taken of the known ability of relatively high intensity bursts of ultrasound to destroy such microbubbles. Thus by comparing the detected light signal (or image) before and after ultrasound exposure mapping the distribution of the contrast agent may be facilitated.

In another embodiment of the invention the contrast medium for imaging modalities based on light will comprise physiologically tolerable particles of lipid materials, e.g. emulsions, especially aqueous emulsions. Preferred are halogen comprising lipid materials. This embodiment of the invention includes, for example, the use in light imaging of fat emulsions (JP 5186372), emulsions of fluorocarbons (JP 2196730, JP 59067229, JP 90035727, JP 92042370, WO 930798, WO 910010, EP 415263, WO 8910118, U.S. Pat. No. 5,077,036, EP 307087, DE 4127442, U.S. Pat. No. 5,114,703), emulsions of brominated perfluorocarbons (JP 60166626, JP 92061854, JP 5904630, JP 93001245, EP 231070), perfluorochloro emulsions (WO 9311868) or other emulsions (EP 321429).

In yet another embodiment of the invention the contrast medium for imaging modalities based on light will comprise physiologically tolerable liposomes. Preferred groups of liposomes are phospholipid liposomes and multilamelar liposomes.

This embodiment of the invention includes, for example, the use in light imaging of phospholipid liposomes containing cholesterol derivatives (U.S. Pat. No. 4,544,545); liposomes associated with compounds containing aldehydes (U.S. Pat. No. 4,590,060); lipid matrix carriers (U.S. Pat. No. 4,610,868); liposomes containing triiodobenzoic acid derivatives of the type also suitable for X-ray examination of liver and spleen (DE-2935195); X-ray contrast liposomes of the type also suitable for lymphography (U.S. Pat. No. 4,192,859); receptor-targeted liposomes (WO-8707150); immunoactive liposomes (EP-307175); liposomes containing antibody specific for antitumor antibody (U.S. Pat. No. 4,865,835); liposomes containing oxidants able to restore MRI contrast agents (spin labels) which have been reduced (U.S. Pat. No. 4,863,717); liposomes containing macromolecular bound paramagnetic ions of the type also suitable for MRI (GB-2193095); phospholipid liposomes of the type also suitable for ultrasound imaging containing sodium bicarbonate or aminomalonate as gas precursor (U.S. Pat. No. 4,900,540); stable plurilamellar vesicles (U.S. Pat. No. 4,522,803); oil-filled paucilamellar liposomes containing non-ionic surfactant as lipid (U.S. Pat. No. 4,911,928); liposomal phospholipid polymers containing ligands for reversible binding with oxygen (U.S. Pat. No. 4,675,310); large unilamellar vesicle liposomes containing non-ionic surfactant (U.S. Pat. No. 4,853,228); aerosol formulations containing liposomes (U.S. Pat. No. 4,938,947 and U.S. Pat. No. 5,017,359); liposomes containing amphipathic compounds (EP-361894); liposomes produced by adding an aqueous phase to an organic lipid solution followed by evaporating the solvent and then adding aqueous lipid phase to the concentrate (FR-2561101); stable monophasic lipid vesicles of the type also useful for encapsulation of bioactive agents at high concentrations (WO-8500751); homogeneous liposome preparations (U.S. Pat. No. 4,873,035); stabilized liposome compounds comprising suspensions in liquefiable gel (U.S. Pat. No. 5,008,109); liposheres (solid hydrophilic cores coated with phospholipid) of the type also suitable for controlled extended release of active compounds (WO-9107171); liposomes sequestered in gel (U.S. Pat. No. 4,708,861); metal chelates bound to liposomes, also suitable for use as MR contrast agents (WO-9114178); lipid complexes of X-ray contrast agents (WO-8911272); liposomes which can capture high solute to lipid ratios (WO-9110422); liposomes containing covalently bound PEG moieties on external surface to improve serum half-life (WO-9004384); contrast agents comprising liposomes of specified diameter encapsulating paramagnetic and/or superparamagnetic agents (WO-9004943); liposomes of the type also suitable for delivering imaging agents to tumours consisting of small liposomes prepared from pure phopholipids (EP-179444); encapsulated X-ray contrast agents such as iopromide in liposomes (U.S. Pat. No. 5,110,475); non-phospholipid liposome compositions (U.S. Pat. No. 5,043,165 and U.S. Pat. No. 5,049,389); hepatocyte-directed vesicle delivery systems (U.S. Pat. No. 4,603,044); gas-filled liposomes of the type also suitable as ultrasound contrast agents for imaging organs (U.S. Pat. No. 5,088,499); injectable microbubble suspensions stabilized by liposomes (WO-9115244); paramagnetic chelates bound to liposomes (U.S. Pat. No. 5,135,737); liposome compositions of the type also suitable for localising compounds in solid tumors (WO-9105546); injectable X-ray opacifying liposome compositions (WO-8809165); encapsulated iron chelates in liposomes (EP-494616); liposomes linked to targeting molecules through disulphide bonds (WO-9007924); and compositions consisting of non-radioactive crystalline X-ray contrast agents and polymeric surface modifiers with reduced particle size (EP-498482). Water soluble compounds which, in simple aqueous solution are not apparently significant light scatterers or absorbers, may become efficient scatterers on incorporation within liposomes. Thus iodixanol (and other soluble iodinated X-ray contrast agents that are commercially available) provides a clear solution on dissolution in water. However when iodixanol is encapsulated in liposomes the resulting particulate product is off-white indicating a significant light scattering capability.

Besides using liposomes as carriers for light imaging contrast agents, it is possible to use simple micelles, formed for example from surfactant molecules, such as sodium dodecyl sulphate, cetyltrimethylammonium halides, pluronics, tetronics etc., as carriers for photolabels which are moderately or substantially water insoluble but are solubilised by the amphiphilic micelle forming agent, e.g. photolabels such as indocyanine green. Similarly peptides such as PEG modified polyaspartic acid (see Kwon et al. Pharm. Res. 10: 970 (1993)) which spontaneously aggregate into polymeric micelles may be used to carry such photolabels. Likewise photolabel carrier aggregate particles can be produced by treatment of polycyclic aromatic hydrocarbons with anionic surfactants (e.g. sodium dodecyl sulphate or sulphated pluronic F108) and subsequent addition of heavy metal ions (e.g. thorium or silver). Such heavy metal treatment gives rise to micelles exhibiting phosphorescent behaviour and these can be used in the present invention without incorporation of a photolabel, especially using a pulsed light source and gated detection of the temporally delayed phosphorescent light.

In a still further embodiment of the invention the contrast medium for imaging modalities based on light will comprise physiologically tolerable particles containing iodine. These particles may for example be particles of a substantially water insoluble solid or liquid iodine-containing compound, e.g. an inorganic or organic compound, in the latter case preferably a triiodophenyl group containing compound, or alternatively they may be aggregate particles (such as liposomes) in which at least one of the components is an iodinated compound. In this case the iodinated compound may be a membrane forming compound or may be encapsulated by the membrane. For example, the use of emulsified iodinated oils (U.S. Pat. No. 4,404,182), particulate X-ray contrast agents (JP 67025412, SU 227529, DE 1283439, U.S. Pat. No. 3,368,944, AU 9210145, EP 498482, DE 4111939, U.S. Pat. No. 5,318,767), iodinated esters (WO 9007491, EP 300828, EP 543454, BE 8161143) and iodinated lipids (EP 294534) are included in this embodiment of the invention.

In a yet still further embodiment of the invention the contrast medium for imaging modalities based on light will comprise physiologically tolerable magnetic particles. The term "magnetic particle" as used here means any particle displaying ferromagnetic, ferrimagnetic or superparamagnetic properties and preferred are composite particles comprising magnetic particles and a physiologically tolerable polymer matrix or coating material, e.g. a carbohydrate and/or a blood residue prolonging polymer such as a poly-alkyleneoxide (e.g. PEG) as described for example by Pilgrimm or Illum in U.S. Pat. No. 5,160,725 and U.S. Pat. No. 4,904,479 e.g. biodegradable matrix/polymer particles containing magnetic materials.

This embodiment of the invention includes, for example, the use in light imaging of magnetic liquid (SU 1187221), ferrite particles coated with a negatively charged colloid (DE 2065532), ferrite particles (U.S. Pat. No. 3832457), liquid microspheres containing magnetically responsive substance (EP 42249), magnetic particles with metal oxide core coated with silane (EP 125995), magnetic particles based on protein matrix (DE 3444939), magnetic vesicles (JP 60255728), magnetic particles (SU 106121), magnetic particles embedded in inert carrier (JP 62167730), ferromagnetic particles loaded with specific antibodies (DE 3744518), superparamagnetic particles coated with biologically acceptable carbohydrate polymers (WO 8903675), polymerized lipid vesicles containing magnetic material (U.S. Pat. No. 4,652,257), superparamagnetic materials in biodegradable matrices (U.S. Pat. No. 4,849,210), biodegradable matrix particles containing paramagnetic or ferromagnetic materials (U.S. Pat. No. 4,675,173), ferromagnetic particles with substances for binding affinity for tissue (WO 8601112), ferrite particles (JP 47016625, JP 47016624), ferromagnetic particles (NL 6805260), magnetic polymer particles (WO 7800005, JP 62204501, JP 94016444, WO 870263), barium ferrite particles (WO 8805337), magnetic iron oxide particles (U.S. Pat. No. 4,452,773), amino acid polymer containing magnetic particles (U.S. Pat. No. 4,247,406), complexed double metal oxide particles (EP 186616), magnetic particles (GB 2237198), encapsulated superparamagnetic particles (WO 8911154), biodegradable magnetic particles (WO 8911873), magnetic particles covalently bond to proteins (EP 332022), magnetic particles with carbohydrate matrix (WO 8301768), magnetic particles with silicon matrix (EP 321322), polymer coated magnetic particles (WO 9015666), polymer-protected collodial metal dispersion (EP 252254), biodegradable superparamagnetic particles (WO 8800060), coated magnetic particles (WO 9102811), ferrofluid (DE 4130268), organometallic coated magnetic particles (WO 9326019) and other magnetic particles (EP 125995, EP 284549, U.S. Pat. No. 5,160,726, EP 516252, WO 9212735, WO 9105807, WO 9112025, WO 922586, U.S. Pat. No. 5,262,176, WO 9001295, WO 8504330, WO 9403501, WO 9101147, EP 409351, WO 9001899, EP 600529, WO 9404197).

The particulate contrast agent used according to the invention may, as mentioned above, be non-photo-labelled or photolabelled. In the latter case this means that the particle either is an effective photoabsorber at the wavelength of the incident light (i.e. carries a chromophore) or is a fluorescent material absorbing light of the incident wavelength and emitting light at a different wavelength (i.e. carries a fluorophore). Examples of suitable fluorophores include fluorescein and fluorescein derivatives and analogues, indocyanine green, rhodamine, triphenylmethines, polymethines, cyanines, phalocyanines, naphthocyanines, merocyanines, lanthanide complexes (e.g. as in U.S. Pat. No. 4,859,777) or cryptates, etc. including in particular fluorophores having an emission maximum at a wavelength above 600 nm (e.g. fluorophores as described in WO-A-92/08722). Other labels include fullerenes, oxatellurazoles (e.g. as described in U.S. Pat. No. 4,599,410), LaJolla blue, porphyrins and porphyrin analogues (e.g. verdins, purpurins, rhodins, perphycenes, texaphyrins, sapphyrins, rubyrins, benzoporphyrins, photofrin, metalloporphyrins, etc.) and natural chromophores/fluorophores such as chlorophyll, carotenoids, flavonoids, bilins, phytochrome, phycobilins, phycoerythrin, phycocyanins, retinoic acid and analogues such as retinoins and retinates.

In general, photolabels which contain chromophores should exhibit a large molar absorptivity, e.g. $>10^5$ cm$^{-1}$M$^{-1}$ and an absorption maximum in the optical window 600 to 1300 nm. Particulates for use as noise rejection agents by virtue of their absorption properties should similarly preferably have molar absorptivities in excess of $10^5$ cm$^{-1}$M$^{-1}$ and an absorption maximum in the range 600 to 1300 nm$^{-1}$. For fluorescent particles, the quantum yield for fluorescence is one of the most important characteristics. This should be as high as possible. However the molar absorptivity should also desirably be above $10^5$ cm$^{-1}$M$^{-1}$ for the fluorophore and the absorption maximum should desirably be in the range 600 to 1300 nm for diffuse reflectance studies or 400 to 1300 nm for surface studies.

These photo-labelled materials may be used as such if substantially water-insoluble and physiologically tolerable, e.g. as solid or liquid particles, or alternatively may be conjugated to or entrapped within a particulate carrier (e.g. an inorganic or organic particle or a liposome). Particularly preferred in this are conjugates of formula I $$I_3Ph-L-C^* \qquad (I)$$

where $I_3Ph$ is a triiodophenyl moiety, L is a linker moiety and C* is a chromophore or fluorophore (e.g. as described above). Such compounds form a further aspect of the invention.

The $I_3Ph$ moiety is preferably a 2, 4, 6 triiodo moiety having carboxyl or amine moieties (or substituted such moieties, e.g. alkoxycarbonyl, aminocarbonyl, alkylaminocarbonyl, alkoxycarbonylalkoxycarbonyl, or alkylcarbonylamino groups where the alkyl or alkylene moieties are optionally hydroxy substituted and preferably contain up to 20, particularly 1 to 6, especially 1 to 3 carbons) at the 3 and 5 positions. The linker group L may be any group capable of linking the group C* to the $I_3Ph$ moiety, e.g. an amide, amine, NHSO$_2$ or carboxyl group or a thio analog thereof; or a $C_{1-20}$alkylene chain terminated by such groups and optionally with one or more methylene groups replaced by thia or oxa and optionally substituted for example by thio, oxo, hydroxy or alkyl moieties. Examples of group L include —NHSO$_2$— and —CO$_2$(CH$_2$)$_2$O—CS—NH—.

Such compounds may be prepared by conjugating a chromophoric or fluorophoric molecule to a triiodophenyl compound of the type proposed as X-ray contrast agents by Nycomed, Sterling Winthrop, or Bracco in their numerous patent publications (by way of example U.S. Pat. No. 5,264,610, U.S. Pat. No. 5,328,404, U.S. Pat. No. 5,318,767 and U.S. Pat. No. 5,145,684).

In one particular embodiment of the invention, non-photolabelled particles, e.g. solid particles of a polymer or an iodinated X-ray contrast agent, are provided with a coating or shell of a photolabel, e.g. a fluorescent agent, for example by chemically or physiochemically binding the photolabel to the particles (e.g. by using oppositely charged photolabel and particles). The resulting coated particles, preferably of nano particle size (e.g. 5 to 800 nm, especially 10 to 500 nm) if labelled with a fluorophore would allow light energy trapped by the core to be transferred to the luminescing surface and so enhance light emission by the fluorophore. Compositions containing such particles form a further aspect of the invention.

Alternatively the photo-label may be entrapped within a solid polymer matrix, e.g. by co-precipitation of polymer and photolabel or by precipitation of photo-label within the pores of a porous inorganic or organic matrix.

Suitable organic polymer matrices for use as carriers or cores for photolabels are substantially water insoluble physiologically tolerable polymers, e.g. polystyrene latex, polylactide coglycolide, polyhydroxybutyrate co-valerate etc.

Other physiologically acceptable particles may be used in contrast media for imaging methods based on light in accordance with of the present invention. Preferred groups of materials are e.g. biodegradable polymer particles, polymer or copolymer particles and particles containing paramagnetic materials. The particles can for example be crosslinked gelatin particles (JP 60222046), particles coated with hydrophilic substances (JP 48019720), brominated perfluorocarbon emulsions (JP 58110522), perfluorocarbon emulsions (JP 63060943), particles and emulsions for oral use (DE 3246386), polymer particles (WO 8601524, DE 3448010), lipid vesicles (EP 28917), metal oxide particles (JP 1274768), metal transferrin dextran particles (U.S. Pat. No. 4,735,796), monodisperse magnetic polymer particles (WO 8303920), polymer particles (DE 2751867), microparticles containing paramagnetic metal compounds (U.S. Pat. No. 4,615,879), porous particles containing paramagnetic materials (WO 8911874), hydrophilic polymer particles (CA 1109792), water-swellable polymer particles (DE 2510221), polymer particles (WO 8502772), metal loaded molecular sieves (WO 9308846), barium sulphate particles (SU 227529), metal particles (DE 2142442), crosslinked polysaccharide particles (NL 7506757), biodegradable polymer particles (BE 869107), niobium particles (SU 574205), biodegradable polymer particles (EP 245820), amphiphilic block copolymers (EP 166596), uniform size particles (PT 80494), coloured particles (WO 9108776), polymer particles (U.S. Pat. No. 5,041,310, WO 9403269, WO 9318070, EP 520888, DE 4232755), porous polymer particles (WO 9104732), polysaccharide particles (EP 184899), lipid emulsions (SU 1641280), carbohydrate particles (WO 8400294), polycyanoacrylate particles (EP 64967), paramagnetic particles (EP 275215), polymer nanoparticles (EP 240424), nanoparticles (EP 27596, EP 499299), nanocapsules (EP 274961), inorganic particles (EP 500023, U.S. Pat. No. 5,147,631, WO 9116079), polymer particles ((EP 514790), apatite particles (WO 9307905), particulate micro-clusters (EP 546 939), gel particles (WO 9310440), hydrophilic colloids (DE 2515426), particulate polyelectrolyte complex (EP 454044), copolymer particles (EP 552802), paramagnetic polymer particles (WO 9222201), hydrophilic polyglutamate microcapsules (WO 9402106) and other particles (WO 9402122, U.S. Pat. No. 4,997,454, WO 9407417, EP 28552, WO 8603676, WO 8807870, DE 373809, U.S. Pat. No. 5,107,842, EP 502814).

In general, where the particulate agent is intended for parenteral administration (e.g. into the vasculature), it may be desirable to prolong the blood residence time for the particles by attaching to these a blood residence time prolonging polymer as described for example by Pilgrimm in U.S. Pat. No. 5,160,725 or Illum in U.S. Pat. No. 4,904,479. In this way imaging of the vascular system may be facilitated by delaying the uptake of the particle by the reticuloendothelial system. In the case of liposomal particles, the blood residence prolonging polymer may be bound to preformed liposomes or, conjugated to liposomal membrane forming molecules, may be used as an amphiphilic membrane forming component so resulting in liposomes carrying the hydrophilic blood residence polymer component on their surfaces. Alternatively or additionally the particles may be conjugated to a biotargetting moiety (e.g. as described in WO-A-94/21240) so as to cause the particles to distribute preferentially to a desired tissue or organ, e.g. to tumor tissue.

The particle size utilized according to the invention will depend upon whether particle administration is parenteral or into an externally voiding body cavity and on whether or not the particles are photo-labelled. In general particle sizes will be in the range 5 to 10000 nm, especially 15 to 1500 nm, particularly 50 to 400 nm and for particles which are being used for their scattering effect particle size will preferably be in the range $\frac{1}{15}$ to $2\lambda$, or more preferably $\frac{1}{10}\lambda$ to $\lambda$, especially $\lambda/4\Pi$ to $\lambda/\Pi$, more especially about $\lambda/2\Pi$ (where $\lambda$ is the wavelength of the incident light in the imaging technique). By selecting a particle size which scatters effectively at wavelengths above the absorption maxima for blood, e.g. in the range 600 to 1000 nm, and by illuminating at a wavelength in that range, the contrast efficacy of non-photolabelled particles may be enhanced.

For administration to human or animal subjects, the particles may conveniently be formulated together with conventional pharmaceutical or veterinary carriers or excipients. The contrast media used according to the invention may conveniently contain pharmaceutical or veterinary formulation aids, for example stabilizers, antioxidants, osmolality adjusting agents, buffers, pH adjusting agents, colorants, flavours, viscosity adjusting agents and the like. They may be in forms suitable for parenteral or enteral administration, for example, injection or infusion or administration directly into a body cavity having an external voidance duct, for example the gastrointestinal tract, the bladder and the uterus. Thus the media of the invention may be in conventional pharmaceutical administration forms such as tablets, coated tablets, capsules, powders, solutions, suspensions, dispersions, syrups, suppositories, emulsions, liposomes, etc; solutions, suspensions and dispersions in physiologically acceptable carrier media, e.g. water for injections, will however generally be preferred. Where the medium is formulated for parenteral administration, the carrier medium incorporating the particles is preferably isotonic or somewhat hypertonic.

The contrast agents can be used for light imaging in vivo, in particular of organs or ducts having external voidance (e.g. GI tract, uterus, bladder, etc.), of the vasculature, of phagocytosing organs (e.g. liver, spleen, lymph nodes, etc.) or of tumors. The imaging technique may involve endoscopic procedures, e.g. inserting light emitter and detector into the abdominal cavity, the GI tract etc. and detecting transmitted, scattered or reflected light, e.g. from an organ or duct surface. Where appropriate monochromatic incident light may be utilized with detection being of temporally delayed light emission (e.g. using pulsed light gated detection) or of light of wavelengths different from that of the incident light (e.g. at the emission maximum of a fluorophore in the contrast agent). Similarly images may be temporal images of a selected target demonstrating build up or passage of contrast agent at the target site. The light used may be monochromatic or polychromatic and continuous or pulsed; however monochromatic light will generally be preferred, e.g. laser light. The light may be ultraviolet to near infra-red, e.g. 100 to 1300 nm wavelength however wavelengths above 300 nm and especially 600 to 1000 nm are preferred.

The contrast media of the invention should generally have a particle concentration of $1 \cdot 10^{-6}$ g/ml to $50 \cdot 10^{-3}$ g/ml, preferably $5 \cdot 10^{-6}$ g/ml to $10 \cdot 10^{-3}$ g/ml. Dosages of from $1 \cdot 10^{-7}$ g/kg to $5 \cdot 10^{-1}$ g/kg, preferably $1 \cdot 10^{-6}$ g/kg to $5 \cdot 10^{-2}$ g/kg will generally be sufficient to provide adequate contrast although dosages of $1 \cdot 10^{-4}$ g/kg to $1 \cdot 10^{-2}$ g/kg will normally be preferred.

The various publications referred to herein are hereby incorporated by reference.

The invention is further illustrated by the following non-limiting Examples. Unless otherwise stated percentages and ratios are by weight.

EXAMPLE 1
Iodixanol Containing Liposomes

Liposomes of average diameter 300 to 600 nm are prepared by a modification of the "Thin film hydration method" described by A. D. Bangham et al. "Methods in Membrane Biology (E. D. Korn, ed), Plenum Press, NY, pp 1–68 (1974). The maximum batch size produced by the process is 2.0 L. The hydrogenated phosphatidylcholine (10 g H-PC) and hydrogenated phosphatidyl serine (1 g H-PS) are dissolved in chloroform/methanol/water (4:1:0.025, volume ratios) by shaking in a water bath at 70° C. The solvents are removed by rotary evaporation until a dry mixture of the PLs appear. The phospholipid mixture is added to an aqueous, isotonic solution of iodixanol and tonicity agent at a temperature of 60–70° C., and the mixture is homogenised with a homomixer, (6000 rpm for 10 minutes at a temperature of 65–70° C.). The liposomes formed are extruded once through three polycarbonate filters. 5.0 mL of the liposome suspension are filled in 20 mL glass bottles, closed with grey rubber stoppers and sealed with aluminium capsules. The liposomes are sterilised by autoclaving (at 121° C. for 20 minutes).

EXAMPLE 2
Fat Emulsion

| Fat emulsion | |
| --- | --- |
| An oil-in-water emulsion is prepared from | |
| soybean oil | 10 g |
| safflower oil | 10 g |
| egg phosphatides | 1.2 g |
| glycerin | 2.5 g | water to osmolarity of 258 mOsm/L and pH of 8.3 to 9.0 (Such an emulsion is available commercially under the trade name Liposyn II from Abbott Laboratories, Chicago, Ill., USA). This can be diluted with physiological saline to the desired concentration.

EXAMPLE 3
A. Solid Microparticles

A gas-filled (e.g. air filled) microbubble suspension, with particle size 1 to 12 μm may be prepared with oleic acid and human serum albumin as the microbubble shell material.

A 216 ml sample of a 0.5% aqueous solution of sodium oleate was titrated with 0.1 N HCl so that the final pH was in the range 3.9–4.0. The solution had become very turbid due to the formation of an oleic acid suspension. The particle size as measured by optical microscopy was in the 0.1 micron range.

The suspension was pressurized to increase the solubility of the gas in the oleic acid suspension. The suspension was placed in a 500 ml stirred autoclave (Zipperclave manufactured by Autoclave Engineers, Inc.) fitted with a 6 blade turbine-type impeller (from Dispersimax). The vessel was sealed and charged to 1000 psig air (typical pressure ranges were 900–1100 psig). The suspension was agitated at 1000 rpm (agitation ranged from 750–1500 rpm) for one hour at room temperature (23–25° C.). Typically the temperature rose 2–3° C. during the run. Agitation was stopped, the vessel vented and the suspension was held for 30 minutes before use. The particle size as measured by optical microscopy was in the 0.1 micron range.

2 g of a 25% aqueous solution of human serum albumin (HSA) was added to 28 g of water and 20 g of the emulsion described above. The turbid solution was heated to 65° C. while oxygen gas was bubbled in. The solution was then stirred using an Omni-Stirrer (homogenizer) for 5 minutes at the mid-range setting. The foamy mixture was poured into a separatory funnel and left to stand for 30 minutes. The liquid was removed from the bottom and 10 ml of fresh 1% HSA solution was added to the foam. After 30 minutes the liquid was removed and 10 ml fresh 5% HSA solution was added so that the foam was resuspended in solution. The liquid was quickly collected from the bottom. The particles (microbubbles) had a diameter range of 1–12 microns with a wall thickness of 1–2 microns.

B. Gas Filled Microparticles

Encapsulated gas microspheres may be prepared according to WO-A-95/01187 by mixing an aqueous solution of human serum albumin with a water insoluble gas such as a perfluoroalkane (e.g. dodecafluoropentane).

EXAMPLE 4
Polymer Particles

A polymer particle suspension may be prepared by dissolving the biodegradable polymer polyhydroxybutyrate-co-valerate in a suitable organic solvent such as acetone, methylene chloride and the like, precipitation in water and removal of the organic solvent by vacuum distillation or diafiltration. Particle size may be selected to be within the range 0.05 μm to 10 μm by choice of surfactant stabilizers, rate of solvent evaporation, agitations as is well known in the art.

EXAMPLE 5
Optionally Photolabelled Nanoparticulate Suspensions

A solution of WIN 70177 (an iodinated contrast agent prepared according to Example 24 below) and, optionally fluoroscein in the molar ratio 100:1, optimally 50:1, most optimally 25:1, in DMSO (or DMF) is precipitated in water. The resulting precipitate is milled as described in U.S. Pat. No. 5,145,684 together with a surfactant stabilizer (eg. Pluronic F108 or Tetronic T-908 or 1508) to a particle size of 0.2 μm and dispersed in an aqueous medium to a contrast agent concentration of 0.5 to 25% by weight and a surfactant content of 0.1 to 30% by weight. A cloud point modifier such as polyethylene glycol 400 (PEG 400) or propylene glycol as disclosed in U.S. Pat. No. 5,352,459 may also be included to ensure stability on autoclave stabilization.

EXAMPLE 6
Photolabelled Nanoparticulate Suspensions

Phytochrome is added to an aqueous solution of sodium dodecyl sulphate (pH >10). The resulting solution is added to a stirred solution of acetic acid containing a surfactant (selected from PVP, pluronics and tetronics) and the mixture is diafiltered to remove soluble salts, excess acid etc. from the suspension yielding a dispersion of 10–100 nm particles.

EXAMPLE 7
Photolabelled Micelles

Indocyanine green (ICG) (0.1 to 10%) is mixed with 3% Pluronic F108 in aqueous solution to form a micellar composition which is sterile filtered.

The ICG content used may be high (>0.5%) to produce mixed micelles or low (<0.5%) to produce micellar solutions of ICG. ICG-concentrations of 0.2 to 0.5% are preferred.

EXAMPLE 8
Photo-Labelled Liposomes

A liposome suspension is prepared using a 0.01 M solution of indocyanine green and 5 to 10% of a phospholipid (10:1 ratio of lecithin to dipalmitoylphosphatidyl serine). Preparation is effected by conventional techniques (eg. ultrasound) followed by extrusion through controlled pore size filters and diafiltration or microfluidisation. The resulting liposomes are steam sterilizable and are sterile filterable and have demonstrated physical stability under nitrogen for over six months.

EXAMPLE 9
Photo-Labelled Emulsions

An oil in water emulsion is prepared from 10 g safflower oil, 10 sesame oil, 1.2 g egg phosphatides, 2.5 g glycerin, 0.5 to 10 g photo-label (eg. fluorescein or indocyanine green) and water to 100 g total. Emulsification is effected by conventional means and the resultant emulsion is sterile filtered through 0.2 μm sterile filters or steam sterilized using conventional means.

EXAMPLE 10
Particulate Iodinated Compounds

WIN 70146 (an iodinated X-ray contrast agent prepared according to Example 23 below) was added to each of 3×1.5 oz brown glass bottles containing approximately 12 ml of zirconium silicate, 1.1 mm diameter beads in an amount sufficient to be 15% (wt/vol %) of the final suspension. Bottle A was also made 3% (wt/vol %) Pluronic F-68 while bottle B was made 3% (wt/vol %)) Pluronic F-108 and bottle C was made 3% (wt/vol %) Tetronic T-908. The resulting suspensions were milled at approx 150 rpm for a total of 9 days with estimates of particle size determined at various intervals as detailed below.

| Days of milling | Average Particle Size (nm) | | |
|---|---|---|---|
| | F-68 | F-108 | T-908 |
| 2 | 1939* | 158 | 162 |
| 3 | 223 | 161 | 162 |
| 7 | 157 | 158 | 156 |

| Days of milling | Average Particle Size (nm) | | |
|---|---|---|---|
| | F-68 | F-108 | T-908 |
| 9 | 158 | 159 | 159 |
| After 1 week at room temperature | 166 | 166 | 161 |
| After autoclaving at 121 degrees C. for 20 min.+ | 181 | 190 | 183 |

*Dioctysulfosuccinate sodium (DOSS) was added at this point to aid in milling in an amount equal to 0.2% (wt/vol %).
+DOSS was added to the F108 and T908 samples for autoclaving as a cloud point modifier (at 0.2%, wt/vol %).

These data demonstrate the unexpected ease of small particle preparation with this agent (ie. WIN 70146) in both F108 and T908 as well as excellent stability to heat (autoclaving) and time on the shelf.

EXAMPLE 11
Preparation and Acute Safety Testing of Nanoparticle Suspensions of WIN 70146 in Pluronic F108

WIN 70146 was prepared as in Example 10 and injected into the tail vein of mice at doses of 3 ml/kg, 15 ml/kg, and 30 ml/kg (ie. 0.45 gm/kg, 2.25 gm/kg and 4.5 gm/kg). No untoward effects were noted in any of the mice at any dose for a period of 7 days after which time the animals were sacrificed. Gross observation of these animals did not reveal any obvious lesions or disfigurations.

Further in depth safety studies in rats have not revealed significant safety issues due to a single dose of WIN 70146/F108 at levels up to and including 30 ml/kg (4.5 gm/kg). These studies included in-depth histopathology, clinical chemistry, and in life observations.

EXAMPLE 12
Preparation of WIN 70146 in Pluronic F108 (I-404)

WIN 70146 was milled with 1.1 mm diameter zirconium silicate beads for 3 days under aseptic conditions. The concentration of this agent was 15% WIN 70146 in the presence of 4% Pluronic F-108. No additional salts or surfactants were added. The average particle size of the resulting nanoparticle suspension was 162 nm as determined by light scattering.

EXAMPLE 13
Preparation of an Autoclavable Formulation of WIN 70146 using Pluronic F-108 and PEG 400

WIN 70146 was milled with 1.1 mm diameter zirconium silicate beads in the presence of Pluronic F-108 for 3 days. The final particle size was determined to be 235 nm. At this point, sterile PEG 400 was added to the suspension such that at completion, the formulation contained 15% (wt/vol %) WIN 70146, 3% (wt/vol %) Pluronic F-108 and 10% PEG 400. This formulation was then autoclaved under standard conditions (ie. 121 degrees C for 20 min.) resulting in a final particle size of 248 nm.

EXAMPLE 14
Demonstration of Light Scattering above Incident Wavelengths of 600 nm by Nanoparticle Suspensions of WIN 70146

A nanoparticle suspension of WIN 70146 was prepared as in Example 10 using 4.25% F108/10% PEG 400 which after autoclaving resulted in particles with an average diameter of 228 nm. This suspension was then diluted in water to various levels listed below. The percent of incident light transmitted was then determined for each suspension at several wavelengths (see below). The suspensions were then dissolved by addition of methanol and examined for percent transmitted light against an equivalent solvent blank. The results are given below.

Per Cent Transmission at 632 nm, 700 nm and 820 nm of Both NanoParticulate WIN 70146 and Dissolved WIN 70146

| Sample | % T suspension | | | % T solution | | |
|---|---|---|---|---|---|---|
| Conc | 632 nm | 700 nm | 820 nm | 632 nm | 700 nm | 820 nm |
| 0.015% | 54.7 | 64.5 | 77.0 | 100.4 | 100.3 | 100.5 |
| 0.0375% | 25.4 | 36.6 | 53.8 | 99.9 | 99.9 | 99.9 |
| 0.075% | 7.7 | 15.4 | 31.8 | 99.9 | 99.8 | 99.9 |
| 0.150% | 0.5 | 1.9 | 8.6 | 41.4* | 51.9* | 66.2* |
| 0.300% | 0.0 | 0.1 | 0.8 | 1.2* | 4.0* | 13.5* |

*These samples were not fully dissolved and showed visible turbidity

These results demonstrate that the suspensions are efficient light scattering agents which do not absorb significant amounts of incident light in these wavelength regions (ie., dissolved WIN 70146 does not absorb light above 600 nm). Additional examination of the absorbance vs wavelength for the dissolved agent does not show any evidence of light absorbance from 600 to 800 nm while the nanoparticle agent shows a classic absorbance decay due to scattering of the incident light.

EXAMPLE 15

Preparation of Nanoparticle Suspension of WIN 70177

A formulation of WIN 70177 (an iodinated X-ray contrast agent prepared according to Example 24) was prepared as 15 gm of WIN 70177/100 ml of suspension and 4.25 gm of Pluronic F108/100 ml of suspension and 10 gm of PEG 400/100 ml of suspension. The suspension was milled for 5 days after which the average particle size was determined by light scattering to be about 235 nm. Stability testing in fresh rat plasma and simulated gastric fluid did not show any aggregation.

EXAMPLE 16

Demonstration of Light Scattering above Incident Wavelengths of 600 nm by Nanoparticulate WIN 70177

A nanoparticle suspension of WIN 70177 was prepared as in Example 15 using 4.25% F108/10% PEG 400 which after autoclaving resulted in particles with an average diameter of 236 nm. This suspension was then diluted in water to various levels listed below. The percent of incident light transmitted was then determined for each suspension at several wavelengths (see below). The suspensions were then dissolved by addition of methanol and examined for percent transmitted light against an equivalent solvent blank. The results are given below.

Per Cent Transmission at 632 nm and 700 nm of Both Nanoparticulate WIN 70177 and Dissolved WIN 70177

| Sample | % T suspension | | | % T solution | | |
|---|---|---|---|---|---|---|
| Conc | 632 nm | 700 nm | 800 nm | 632 nm | 700 nm | 800 nm |
| 0.015% | 53.3 | 62.8 | 73.1 | 102.2 | 101.9 | 101.8 |
| 0.0375% | 34.6 | 45.7 | 59.1 | 102.3 | 101.9 | 101.8 |
| 0.075% | 25.8 | 36.8 | 51.1 | 100.9 | 100.8 | 101.0 |
| 0.150% | 6.7 | 13.6 | 26.3 | 59.5* | 67.8* | 77.0* |
| 0.300% | 0.1 | 0.6 | 3.2 | 7.4* | 14.4* | 26.8* |

*Did not fully dissolve; particles still present.

These data demonstrate the scattering abilities of the particulate form of WIN 70177 while the dissolved material does not absorb any energy over the wavelength of light examined. Further, an examination of the absorbance due to the particulate WIN 70177 and that due to the dissolved WIN 70177 shows that the particulate material provides an exponential drop in absorbance with wavelength as would be expected for scattering due to suspended particles while the soluble material has virtually no absorbance at all even at 5 times the concentration.

EXAMPLE 17

Preparation of a Nanoparticle Suspension of WIN 67722

A formulation of WIN 67722 (an iodinated X-ray contrast agent as described in U.S. Pat. No. 5,322,679) was prepared as in Example 1 using 3% Pluronic F108 and 15% PEG 1450. The suspension was milled for 3 days and achieved a particle size of 213 nm (small fraction at 537 nm) as determined by light scattering with a Coulter N4MD particle sizer.

EXAMPLE 18

Demonstration of Light Scattering above Incident Wavelengths of 600 nm by Nanoparticulate WIN 67722

A nanoparticle suspension of WIN 67722 was prepared as in Example 17 using 3% Pluronic F108 and 15% PEG 1450 which after autoclaving gave particles with an average diameter of 214 nm. This suspension was then diluted in water to various levels listed below. The percent of incident light transmitted was then determined for each suspension at several wavelengths (see below). The suspensions were then dissolved by addition of methanol and examined for percent transmitted light against an equivalent solvent blank. The results are given below.

Per Cent Transmission at 632 nm and 700 nm of Both NanoParticulate WIN 67722 and Dissolved WIN 67722

| Sample | % T suspension | | | % T solution | | |
|---|---|---|---|---|---|---|
| Conc | 632 nm | 700 nm | 820 nm | 632 nm | 700 nm | 820 nm |
| 0.015% | 47.9 | 57.1 | 69.2 | 99.9 | 99.9 | 100.6 |
| 0.0375% | 20.5 | 29.9 | 45.6 | 100.2 | 100.2 | 100.4 |
| 0.075% | 4.8 | 9.9 | 22.1 | 100.1 | 100.2 | 100.4 |
| 0.150% | 0.2 | 1.0 | 4.9 | 48.2* | 55.3* | 65.5* |
| 0.300% | 0.0 | 0.0 | 0.2 | 1.3* | 3.5* | 10.7* |

*Did not fully dissolve; particles still present

These data demonstrate the scattering abilities of the particulate form of WIN 67722 while the dissolved material does not absorb any energy over the wavelength of light examined. Further, an examination of the absorbance due to the particulate WIN 67722 and that due to the dissolved WIN 67722 shows that the particulate material provides an exponential drop in absorbance with wavelength as would be expected for scattering due to suspended particles while the soluble material has virtually no absorbance at all even at 5 times the concentration.

EXAMPLE 19
Preparation of Nanoparticle Suspension of WIN 72115

Nanoparticle WIN 72115 (a fluorescent iodinated contrast agent as described in Example 21 below) was prepared by combining WIN 72115 and Pluronic F108 (BASF, Parsippany, N.J.) in a glass jar at concentrations of 15 gm/100 ml suspension and 3 gm/100 ml suspension. The jar was then half filled with 1.0 mm diameter zirconium silicate beads and sufficient water added to complete the required concentrations of agent/surfactant as noted above. Alternatively, the surfactant can be dissolved in the water before addition to the jar (with or without sterile filtration through 0.2 micron filters).

The jar is then rolled on its side for not less than 24 hours or more than 14 days at a rate of rotation sufficient to cause the beads within the jar to "cascade" down the walls of the jar as it turns (see U.S. Pat. No. 5,145,684). At the end of the milling cycle, the material is harvested from the jar and separated from the milling beads.

Nanoparticles of WIN 72115 prepared in this manner have an average particle size of 225 nm by light scattering.

WIN 72115 was designed to be excited with incident radiation from an Argon Ion laser (in the green, near 514 nm) and emit light at wavelengths above that value. Thus, after injection, illumination of the patient with green light would stimulate emission of light of a slightly different wavelength that could be used for diagnostic purposes. The key features of this agent are that it can be prepared as nanoparticles, remain within the vasculature for greater than 15 minutes, provide both scattering and fluorescence contrast for light imaging.

In place of WIN 72115, the photolabelled agent of Example 22 below may be used.

EXAMPLE 20
Light Scattering from Polymeric Particles—Dependence upon Particle Size and Concentration Three samples of polystyrene latex particles were diluted to various extents and examined for their effects upon transmitted light at several different wavelengths. The results confirm that larger particles and higher concentrations result in better scattering of the incident light.

| Sample | concentration (Wt/vol %) | Per cent Transmission | | |
|---|---|---|---|---|
| | | 600 nm | 700 nm | 820 nm |
| 170 nm | .0025 | 97.9 | 98.3 | 98.7 |
| | .025 | 94.8 | 96.3 | 97.4 |
| | .075 | 89.3 | 92.8 | 95.2 |
| 300 nm | .0025 | 99.3 | 99.5 | 99.6 |
| | .025 | 92.4 | 94.5 | 95.8 |
| | .075 | 83.1 | 88.3 | 91.8 |
| 500 nm | .0025 | 98.8 | 99.1 | 99.4 |
| | .025 | 88.1 | 91.4 | 93.9 |
| | .075 | 68.3 | 76.5 | 83.0 |

EXAMPLE 21
3-(N-Acetyl-N-ethylamino)-5-[(5-dimethylamino-1-naphthylsulfonyl)amino]-2,4,6-triiodobenzoic Acid Ethyl Ester (WIN 72115)

To a stirred solution of ethyl 3-(N-acetyl-N-ethylamino)-5-amino]-2,4,6-triiodobenzoate (11.6 g, 18.5 mmol) in pyridine (75 ml) cooled in ice bath is added 60% NaH/oil dispersion (1.8 g, 46.3 mmol). After the reaction of NaH with the amino group is over, dansyl chloride (5 g, 18.8 mmol) is added. The resulting reaction mixture is stirred in ice bath for 4 hours and at room temperature for 20 hours. After quenching with acetic acid (10 ml), the brown solution is concentrated on a rotary evaporator. The brown residue is first washed with hexanes and then slurried in water (200 ml). The resulting dirty yellow gummy solid is collected, washed with water, dried, and recrystallized from ethanol to provide 5.3 g (33%) of bright yellow crystals: mp 238–240° C., ms (FAB) 862 (90%, MH). Anal. Calcd. for $C_{25}H_{26}I_3N_3O_5S$: C, 34.86; H, 3.05; N, 4.88; I, 44.20. Found: C, 34.91; H, 3.02; N, 4.74; I, 44.53. $^1$H-NMR and $^{13}$C-NMR spectra are consistent with the structure:

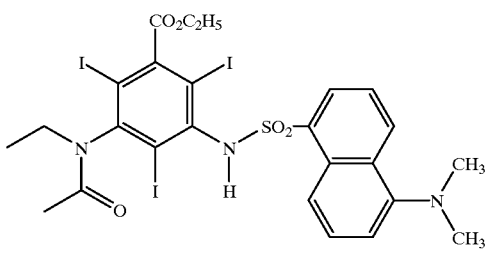

EXAMPLE 22
2-(3,5-Bisacetylamino-2,4,6-triiodobenzoyloxy)ethyl N-Fluoreceinylthiocarbamate A mixture of 2-hydroxyethyl 3,5-(bisacetylamino)-2,4,6-triiodobenzoate (0.658 g, 1 mmol), fluorecein isothiocynate (0.389 g, 1 mmol), 60% NaH/oil dispersion (0.24 g, 6 mmol) and DMF (25 ml) is stirred at ambient temperature for 26 hours and then quenched with 6N HCl (2.5 ml). The resulting mixture is concentrated on a rotary evaporator under reduced pressure. The yellow solid residue is washed with water and recrystallized from DMF to yield yellow crystals of the product in 65% yield. Elemental analysis and spectral data are consistent with the structure:

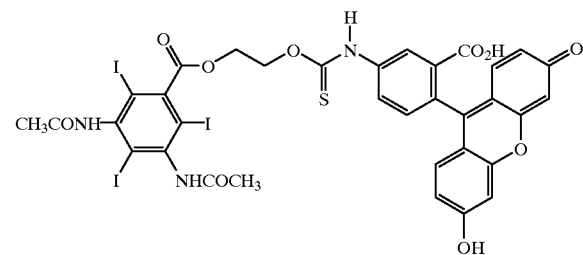

EXAMPLE 23
Benzoic acid, 3,5-bis(acetylamino)-2,4,6-triiodo-1-(ethoxycarbonyl)pentyl ester (WIN 70146)

To a stirred solution of sodium diatrizoate (150 g, 235.2 mmole) in dry DMF (1200 ml) at room temperature, was added ethyl 2-bromohexanoate (63.8 g, 285.8 mmole, 1.09 eq.). The solution was heated overnight at 90° C., then cooled to 60° C. The reaction mixture was then poured into 20l of water with stirring. The resulting white precipitate was collected by filtration and dried at 90° C. under high vacuum. The crude material was recrystallized from DMF/water to give, after drying, analytically pure product; mp 263–265° C. The MS and $^1$H-NMR (300 MHz) spectral data were consistent with the desired structure.

Calculated for $C_{19}H_{23}I_3N_2O_6$: C 30.15, H 3.04, N 3.70, I 50.35

Found: C 30.22, H 3.00, N 3.66, I 50.19

EXAMPLE 24

Propanedioic acid, [[3,5-bis(acetylamino)-2,4,6-triiodobenzoyl]oxy]methyl-bis(1-methylethyl)ester (WIN 70177)

To a stirred mixture of sodium diatrizoate (393 g, 616 mmole) in 500 ml of DMSO at room temperature, was added 173 g (616 mmol) of diisopropyl 2-bromo-2-methylmalonate and the solution was heated at 90–100° C. under an atmosphere of argon for 56 hours. After cooling, the solution was slowly added to 10l of water with mechanical overhead stirring. The precipitated solid was allowed to settle for 6 hours and then collected by filtration. The crude product was washed thoroughly with water (4l) and dried at room temperature overnight. The solid was digested with a solution of potassium bicarbonate (3 g in 700 ml of water containing 15 ml of isopropanol), water and then air dried for 12 hours. Recrystalization from DMF followed by washing with water and drying under high vacuum gave 255 g (51%) of analytically pure product; mp 258–260° C. The MS and $^1$H-NMR (300 MHz) spectral data were consistent with the desired structure.

Calculated for $C_{21}H_{25}I_3N_2O_8$: C 30.98, H 3.10, N 3.44, I 46.76

Found: C 30.96, H 3.00, N 3.44, I 46.77

EXAMPLE 25

In vivo Light Imaging Studies

A. Particulate Scattering Agents

A suspension of multilamellar liposomes formed in a solution of 40% (wt/vol %) iodixanol were injected into white rats which had been implanted with a hepatoma 9L tumor on their rear flank. The injection was imaged using a time gated diode laser incident at 780 nm with detection of the scattering component at 180 degrees to the incident light using fiber optic cables and a phase sensitive detection device in the laboratory of Dr. Britton Chance at the University of Pennsylvania. The liposome particles enhanced scattering in the tumor over the background signal by more than 4× at the dose administered (i.e. 3 ml/kg). While not optimized, these data indicate the feasibility of contrast by scattering agents for light imaging.

B. Fluorescent Particles for Light Imaging Contrast

A suspension of liposomes were prepared in the presence of 0.7 micrograms/ml of indocyanine green (ICG) and sterilized using steam and pressure. The resulting particles had an average diameter of approximately 120 nm as determined by light scattering using a Horiba 910 particle sizing instrument. Upon injection into the rat flank tumor model, these liposomes afforded significantly longer residence in the tumor of the fluorescent agent (i.e. the ICG) than observed with a homogeneous solution of ICG alone. This is useful for imaging in that signal averaging techniques can be applied to enhance the image as well as to mark sites of leaky vasculature. These studies were also carried out at the University of Pennsylvania in the laboratory of Dr. Britton Chance.

EXAMPLE 26

Use of Contrast Media for Enhancement of Laser Doppler Measurement of Blood Flow in the Skin Approximately 0.5 to 1 hour before the measurements are to be made, a sterile aqueous suspension containing 5–20 mg of suspended particles of a dye (e.g. 3,3'-diethylthiatricarbocyanine iodide) with an absorbing maximum between 600 and 1300 nm is administrated by intravenous injection. The mean particle size is preferably about 800 nm and as suspension medium is preferably used physiological saline.

The measurement of blood flow is made after the concentration of contrast agent particles in the blood has stabilized. Measurement may be made with a standard laser Doppler instrument, for example that from Lisca Development AB, Kinkoping, Sweden, that optionally may be modified to incorporate a laser source operating at 830 or 780 nm (see Abbot et al., J. Invest. Dermatol., 107: 882–886 (1996)).

EXAMPLE 27

Use of Contrast Media for Enhancement of Measurement of Blood Flow Through the Skin with Confocal Microscopy Approximately 0.5 to 1 hour before the measurements are to be made, a sterile aqueous suspension containing 5–20 mg of dye (e.g. 3,3'-diethylthiatricarbocyanine iodide) with an absorbing maximum between 600 and 1300 nm is administrated by intravenous injection. The mean particle size is preferably about 800 nm and as suspension medium is preferably used physiological saline.

The measurement of blood flow is made by following the movement of the particles through the capillaries with the confocal microscope.

What is claimed is:

1. A method of generating an image of the human or non-human animal body by in vivo diagnostic light imaging, characterized in that a physiologically tolerable particulate contrast agent comprising a compound of formula

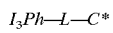

wherein $I_3$Ph is a triiodophenyl moiety, L is a linker and C* is a chromophore or fluorophore is administered into said body and an image of at least part of said body containing said contrast agent is generated.

2. A method as claimed in claim 1 wherein said image is a spatial image.

3. A method as claimed in claim 1 wherein said image is a temporal image.

4. A method as claimed in claim 1 wherein said image is generated from light transmitting through at least part of said body.

5. A method as claimed in claim 1 wherein said image is generated from light reflected from at least part of said body.

6. A method as claimed in claim 1 wherein said image is generated from fluorescence emitted by said agent.

7. A method as claimed in claim 1 wherein said image is of vasculature in said body.

8. A method as claimed in claim 1 wherein said image is of a phagocytic organ in said body.

9. A method as claimed in claim 1 wherein light is emitted and detected endoscopically.

10. A method as claimed in claim 1 wherein said body is irradiated with monochromatic light.

11. A method as claimed in claim 1 wherein the particle size of said particulate agent is from $\lambda/4\Pi$ to $\lambda/\Pi$, where $\lambda$ is the wavelength of said monochromatic light.

12. A method as claimed in claim 11 wherein said particle size is about $\lambda/2\Pi$.

13. A method as claimed in claim 1 wherein said agent further comprises gas-microbubbles.

14. A method as claimed in claim 1 wherein said agent further comprises solid or liquid particles.

15. A method as claimed in claim 1 wherein said agent further comprises liposomes.

16. A method as claimed in claim 1 wherein said chromophore or fluorophore has a molar absorptivity of at least $10^5$ cm$^{-1}$M$^{-1}$ and an absorption maximum in the range 300 to 1300 nm.

17. A method as claimed in claim 16 wherein said particulate agent further comprises liposomes.

18. A method as claimed in claim 16 wherein said particulate agent further comprises solid or liquid particles.

19. A method as claimed in claim 16 wherein said particulate agent further comprises solid particles coated with said compound.

20. A method as claimed in claim 16 wherein said particulate agent further comprises micelles.

21. A method as claimed in claim 1 wherein said image is generated by a light imaging technique selected from confocal scanning laser microscopy, optical coherence tomography, and laser doppler and laser speckle techniques.

22. A method as claimed in claim 21 wherein said body is illuminated with light of a wavelength in the range 600 to 1300 nm and said image is generated using directed scattered light of a wavelength in the range 600 to 1300 nm.

23. A method as claimed in claim 22 wherein the particles of said particulate agent have a mean particle size in the range 600 to 1300 nm.

24. A method as claimed in claim 23 wherein the coefficient of variation of the particle size of said particles is less than 10%.

25. A method as claimed in claim 21 wherein said image is an image of a part of said body no more than 1 mm below an exposed or endoscopically accessed surface thereof.

26. A method as claimed in claim 25 wherein said image is an image of part of the skin.

27. A method as claimed in claim 25 wherein said image is an image of a part of said body no more than 1 mm below a surgically exposed surface.

28. A method as claimed in claim 21 wherein said particles are selected from polymer particles, dyestuff particles, and iodinated organic compound particles.

29. A method as claimed in claim 1 wherein said compound is 3- (N-acetyl-N-ethylamino)-5-[(5-dimethylamino-1-naphthylsulfonyl)amino]-2,4,6-triiodobenzoic acid ethyl ester.

30. A method as claimed in claim 1 wherein said compound is 2- (3,5-bisacetylamino-2,4,6-triiodobenzoyloxy) ethyl N-fluoresceinylthiocarbamate.

31. A method as claimed in claim 1 wherein the contrast agent is present in a nanoparticle suspension.

* * * * *